(12) United States Patent
Green

(10) Patent No.: US 12,121,537 B2
(45) Date of Patent: *Oct. 22, 2024

(54) DIETARY SUPPLEMENTS

(71) Applicant: RHA INVESTMENT LIMITED, Galway (IE)

(72) Inventor: Shawn J. Green, Sacramento, CA (US)

(73) Assignee: RHA INVESTMENT LIMITED, Galway (IE)

( * ) Notice: Subject to any disclaimer, the term of this patent is extended or adjusted under 35 U.S.C. 154(b) by 0 days.

This patent is subject to a terminal disclaimer.

(21) Appl. No.: 17/936,361

(22) Filed: Sep. 28, 2022

(65) Prior Publication Data

US 2023/0233599 A1 Jul. 27, 2023

Related U.S. Application Data

(63) Continuation of application No. 16/818,169, filed on Mar. 13, 2020, now Pat. No. 11,478,506, which is a continuation of application No. 15/814,035, filed on Nov. 15, 2017, now Pat. No. 10,624,921.

(60) Provisional application No. 62/422,353, filed on Nov. 15, 2016.

(51) Int. Cl.

| | |
|---|---|
| *A61K 36/00* | (2006.01) |
| *A23L 33/00* | (2016.01) |
| *A23L 33/105* | (2016.01) |
| *A23L 33/15* | (2016.01) |
| *A23L 33/16* | (2016.01) |
| *A61K 9/00* | (2006.01) |
| *A61K 9/20* | (2006.01) |
| *A61K 31/375* | (2006.01) |
| *A61K 31/51* | (2006.01) |
| *A61K 31/519* | (2006.01) |
| *A61K 31/714* | (2006.01) |
| *A61K 33/00* | (2006.01) |
| *A61K 33/06* | (2006.01) |
| *A61K 36/185* | (2006.01) |
| *A61K 36/21* | (2006.01) |
| *A61K 36/74* | (2006.01) |
| *A61K 47/02* | (2006.01) |
| *A61K 47/12* | (2006.01) |
| *A61K 47/38* | (2006.01) |
| *A61K 47/46* | (2006.01) |

(52) U.S. Cl.
CPC ............ *A61K 33/00* (2013.01); *A23L 33/105* (2016.08); *A23L 33/15* (2016.08); *A23L 33/16* (2016.08); *A23L 33/30* (2016.08); *A61K 9/0056* (2013.01); *A61K 9/0095* (2013.01); *A61K 9/2054* (2013.01); *A61K 9/2068* (2013.01); *A61K 31/375* (2013.01); *A61K 31/51* (2013.01); *A61K 31/519* (2013.01); *A61K 31/714* (2013.01); *A61K 33/06* (2013.01); *A61K 36/185* (2013.01); *A61K 36/21* (2013.01); *A61K 36/74* (2013.01); *A61K 47/02* (2013.01); *A61K 47/12* (2013.01); *A61K 47/38* (2013.01); *A61K 47/46* (2013.01); *A23V 2002/00* (2013.01)

(58) Field of Classification Search
None
See application file for complete search history.

(56) References Cited

U.S. PATENT DOCUMENTS 8,962,038 B2 * 2/2015 Bryan .................. A61K 31/375
424/718
2016/0303177 A1 * 10/2016 Bailey .................. A61K 31/122

FOREIGN PATENT DOCUMENTS

WO WO-2014201360 A1 * 12/2014 ............... A23G 1/00

* cited by examiner

*Primary Examiner* — Susan T Tran
(74) *Attorney, Agent, or Firm* — Squire Patton Boggs (US) LLP

(57) ABSTRACT

Compositions and methods for improving nitric oxide levels in a subject, comprising administering to a subject, a composition comprising dietary nitrate derived from potassium nitrate, beet root (whole plant, powder, plant extract), and/or nitrate-rich leafy green portions (whole plant, powder, plant extract) that improve functional nitric oxide levels in subjects as shown by increasing salivary bioconversion of nitrate to nitrite, a necessary a required step for nitric oxide mediated health benefits. The disclosed novel compositions improve cardiac health, lowers blood pressure, intraocular pressure, and LDL and restores nitric oxide mediated cardiovascular benefits, including but not limited, restoring endothelium function and improving flow mediated dilation.

17 Claims, 2 Drawing Sheets

DIETARY SUPPLEMENTS

CROSS-REFERENCE TO RELATED APPLICATIONS

This application is a continuation of U.S. patent application Ser. No. 16/818,169 filed on Mar. 13, 2020, which is a continuation of U.S. patent application Ser. No. 15/814,035 filed on Nov. 15, 2017, now issued as U.S. Pat. No. 10,624,921, which claims the benefit of U.S. Provisional Application No. 62/422,353 filed on Nov. 15, 2016, each of which is incorporated herein in its entirety by reference.

TECHNICAL FIELD

Embodiments of the present disclosure relate novel dietary supplements for improving nitric oxide levels in individuals.

BACKGROUND

Cardiovascular health is a leading concern around the world. Diseases and disorders ranging from rheumatic heart disease, hypertensive heart disease, ischemic heart disease, cerebrovascular disease and inflammatory heart disease constitute a primary cause of death in both developed and underdeveloped nations. As an advocate of putting cardiovascular disease and its risk factors on the global health agenda, the World Heart Federation strongly supports initiatives addressing obesity, healthy diet and physical activity.

Hypertensive disease generally refers to high blood pressure of unknown origin (primary hypertension) or caused by (secondary hypertension) certain specific diseases or infections, such as tumor in the adrenal glands, damage to or disease of the kidneys or their blood vessels. High blood pressure may overburden the heart and blood vessels and cause disease.

Blood pressure is the force of blood against artery walls as it circulates through the human body. Blood pressure normally rises and falls throughout the day, but it can cause health problems if it stays high for a long time. High blood pressure is sometimes called the "silent killer" because it usually has no warning signs or symptoms: many people do not know that they have high blood pressure, hence the recommendation to have blood pressure checked regularly. According to the CDC, about 70 million American adults (29%) have high blood pressure: that is 1 in every 3 American adults. (Nwankwo T, et al. Hypertension among adults in the US: National Health and Nutrition Examination Survey, 2011-2012. NCHS Data Brief, No. 133. Hyattsville, Md.: National Center for Health Statistics, Centers for Disease Control and Prevention, US Dept of Health and Human Services, 2013). Anyone, including children, can develop high blood pressure. It greatly increases the risk for heart disease and stroke, the first and third leading causes of death in the United States. Blood pressure is an underlying cause of heart attacks, strokes and kidney disease, and the prevalence of high blood pressure is so high, it is considered the single-largest contributor to death worldwide. It is also becoming more resistant to the pharmaceutical drugs used to lower it. In fact, blood pressure remains elevated in nearly one-third of all treated hypertensive patients on pharmaceutical drugs.

Instead of relying on prescriptions, more patients are turning to a healthier eating approach: Keeping sodium intake low and making consumption of nitric oxide-rich vegetables and leafy greens high. This cardio-protective daily diet, known as the DASH (Dietary Approach to Stop Hypertension) Eating Plan, is emerging as an effective way to delay or prevent high blood pressure altogether.

The value of nitric oxide was spotlighted when the Nobel Prize was awarded in 1998 for discovery of this naturally produced cardio-protective factor. A string of clinical studies underscored that vegetables (like red beet roots) and leafy greens (such as spinach and arugula) are replete with nitric oxide. Diets known for promoting heart health and lowering rates of diabetes and obesity, like Japanese diets, Mediterranean diets and plant-based diets, such as DASH, among others including TLC, Ornish, and Mayo, incorporate these natural whole foods. Nitric oxide is emerging as a critically important cardioprotective and vascular wellness factor. With age, arteries lose their elasticity and ability to make nitric oxide to prevent cardiovascular disease. Scientific evidence suggests that vascular aging may be delayed through the increased production of nitric oxide, thereby, enhancing cardiovascular function. Athletes have already taken advantage of these discoveries by increasing their consumption of leafy greens and beetroots, both of which are rich in nitrate, to elevate nitric oxide levels that increase endurance and performance.

A recent study (Apr. 15, 2013) conducted by researchers from Queen Mary University of London, and published in the American Heart Association Journal, Hypertension, provides further support for the importance of nitric oxide and of the blood pressure lowering effects on nitrate-rich vegetables. (Enhanced vasodilator activity of nitrite in hypertension: critical role for erythrocytic xanthine oxidoreductase and translational potential. Ghosh S M et al. Hypertension. 2013 May; 61(5):1091-102. Subjects who drank beetroot juice containing a natural source of inorganic nitrate show an average 10-point decrease in their blood pressure. Sustaining such levels may be critical in maintaining normal blood pressure. The lead author, Dr. Ahiuwalia, reported to Medical Xpress: "our hope is that increasing one's intake of vegetables with a high dietary nitrate content, such as green leafy vegetables or beet root, might be a lifestyle approach that one could easily employ to improve cardiovascular health."

Reducing hypertension would not only improve health outcomes for individual patients, but would also benefit the health system as a whole. Although the percentage of resistance to antihypertensive drugs is relatively lower in the U.S., elevated blood pressure among a rapidly growing number of baby boomers will mean more challenges for health care in the long run unless appropriate measures and lifestyle changes are designed in put in place. Poor diet and physical inactivity remain the primary drivers of cardiovascular disease and metabolic disorders such as gout, obesity, hypertension, and diabetic insulin resistance. A daily lifestyle of a cardioprotective diet, including nitrate-rich plant-based foods, is a solution. More specifically, the amino acid, arginine can be a source for the body to make nitric oxide. Unfortunately, the aging process results in the loss our ability to make nitric oxide through the use of arginine, thereby increasing reliance on a non-arginine source, specifically, dietary nitrate. Plant-based foods, such as the DASH Diet, rich in leafy greens such as arugula, kale, and spinach, help supplement the body's pool of nitrate, which can be converted to nitric oxide, independent of arginine.

DASH holds great promise to fuel compliance, a critical driver to prevent elevated blood pressure, among those living with hypertension. Athletes have already taken advantage of these discoveries by increasing the consumption of nitrate-rich beetroot juices to elevate nitric oxide levels which increases endurance and performance. A growing number of athletes are now validating the nitric oxide potency of their beet juice and modifying their training diets to optimize performance.

But a healthful eating strategy alone will not mean better outcomes for patients without a model to help them break bad habits and support dietary changes on a personal level, one day at a time. Indeed even if individuals and communities have a commitment to healthy diets, the necessary resources may not be readily available due to economics or convenience. For example, some communities may be described as 'food deserts', defined as a region vapid of fresh fruit, vegetables, and other healthful whole foods; often times such food deserts are found in impoverished areas. In other situations, individuals may need to rely on convenience food to ensure sufficient intake of nitrate-rich nutrition, and in such situations it would be useful to have access to nutritional supplements that easy to ingest, transport and store.

What is needed therefore, is nitrate rich dietary supplement. Such supplements should be compatible with day to day conveniences, they should be easy to ingest and they should be palatable. In addition, such supplements should be affordable and preferably derived from natural ingredients.

SUMMARY

Disclosed are novel dietary supplement compositions useful and suitable for improving nitric oxide levels in individuals. In an embodiment, the supplements comprise beet root extract, potassium nitrate, green coffee bean extract, and pomegranate fruit extract. In an embodiment, the supplements further comprise vitamin C, thiamin, folate, vitamin B12 and potassium. The supplements may optionally comprise calcium carbonate, microcrystalline cellulose, coating (polyvinyl alcohol, macrogol, FD&C red #40, talc, titanium dioxide), stearic acid, croscarmellose sodium, magnesium stearate, and silica. The compositions disclosed herein may be suitable for oral ingestion in embodiments known to those skilled in the art, including tablets, chewables, capsules, powders, and the like.

BRIEF DESCRIPTION OF THE DRAWINGS

The accompanying drawings, which are incorporated in and constitute a part of this specification, illustrate several embodiments and together with the description illustrate the disclosed compositions and methods.

DETAILED DESCRIPTION

Figure 1:
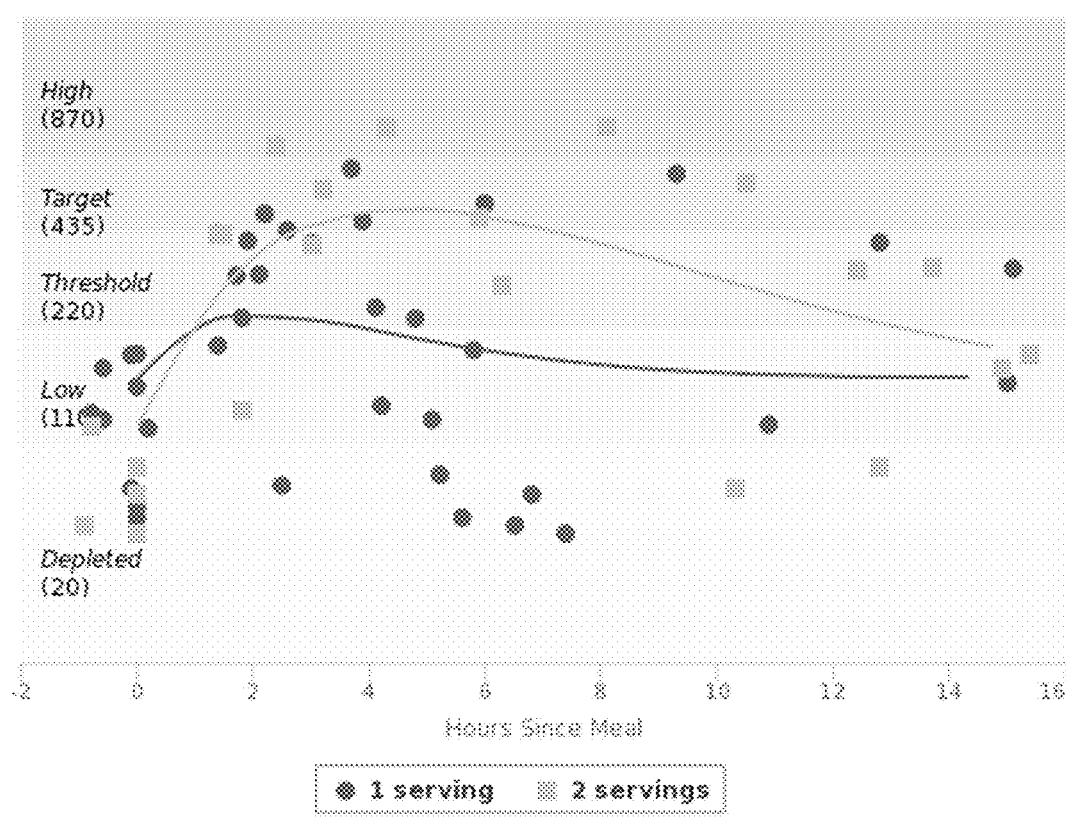
FIG. 1 provides a graph showing the efficacy of the supplements (referred to as servings) as described herein an in the Examples in terms of improving salivary nitric oxide bioavailability. The circles represent one serving and the squares represent two servings.

Before the present compounds, compositions, supplements, and/or methods are disclosed and described, it is to be understood that they are not limited to specific components, or specific ingredients, or production methods unless otherwise specified, or to particular reagents unless otherwise specified, as such may, of course, vary. It is also to be understood that the terminology used herein is for the purpose of describing particular embodiments only and is not intended to be limiting. The following detailed description is exemplary and explanatory and is intended to provide further explanation of the present disclosure described herein. Other advantages, and novel features will be readily apparent to those skilled in the art from the following detailed description of the present disclosure. Texts and references mentioned herein are incorporated in their entirety, including U.S. Provisional Patent Application Ser. No. 62/422,353 filed on Nov. 15, 2016.

Definitions

As used in the specification and the appended claims, the singular forms "a," "an" and "the" include plural references unless the context clearly dictates otherwise. Thus, for example, reference to "a pharmaceutical carrier" includes mixtures of two or more such carriers, and the like.

Ranges can be expressed herein as from "about" one particular value, and/or to "about' another particular value. When such a range is expressed, another embodiment includes from the one particular value and/or to the other particular value. Similarly, when values are expressed as approximations, by use of the antecedent "about," it will be understood that the particular value forms another embodiment.

It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed.

It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15.

It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

Compositions

Disclosed are components to be used to prepare the disclosed compositions as well as the compositions themselves to be used within the methods and compositions disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular compound is disclosed and discussed and a number of modifications that can be made to a number of components including the compound are discussed, specifically contemplated is each and every combination and permutation of the components and the modifications that are possible unless specifically indicated to the contrary. Thus, if a class of components A, B, and C are disclosed as well as a class of components D, E, and F and an example of a combination component, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

The present invention comprises novel nutritional supplements comprising dietary nitrate, wherein said compositions are useful in achieving and maintaining desired nitric oxide levels in subjects, and wherein said compositions may also be useful in restoring functional nitric oxide levels in nitric oxide-deficient subjects by increasing salivary bioconversion of nitrate to nitrite. The compositions may also lower blood pressure, and/or restore nitric oxide mediated cardiovascular benefits, including but not limited to aspects such as restoring endothelium function (i.e, flow mediated dilation). The dietary nitrate of the disclosed compositions may be derived from potassium nitrate, beet root (whole plant, powder, extract), leafy greens (including, but not limited to spinach, kale) or other nitrate-rich leafy plant portions (whole plant, powder). In an embodiment, the nitrate is present in a concentration of 2-20 mmol nitrate per daily dose, the nitrate is in a purified potassium salt form and/or derived from a plant leafy as a whole or powder form. The compositions herein are effective in elevating the saliva conversion of nitrate to nitrite to at least 300 µM. Furthermore, the compositions are effective in reducing systolic blood pressure: in an embodiment, the systolic blood pressure of a pre-hypertensive or hypertensive subject is reduced by 2-11 mmHg within approximately 3 hours and may be sustained within 2-11 mmHg range for a finite period of time.

In certain embodiments, the compositions disclosed herein further comprise vitamin C (ascorbic acid), thiamin (thiamin mononitrate), folate (folic acid), vitamin B12 (methylcobalamin) and potassium. In certain embodiments of the composition, vitamin C (ascorbic acid) comprises 1-2,000 mg, thiamin (thiamin mononitrate) comprises 1-800 mg, folate (folic acid) comprises 1-500 mcg, vitamin B12 (methylcobalamin) comprises 1-500 mcg, and potassium comprises 1-500 mg. In certain embodiments, vitamin C (ascorbic acid) comprises 110 mg, thiamin (thiamin mononitrate) comprises 90 mg, folate (folic acid) comprises 200 mcg, vitamin B12 (methylcobalamin) comprises 200 mcg, and potassium comprises 120 mcg. In addition, the compositions comprise beet root extract, beet root (whole plant, powder, extract), leafy greens (whole plant, powder, extract), coffee bean extract, and pomegranate fruit extract and in certain embodiments further comprise absorbable dietary magnesium The disclosed compositions comprise embodiments wherein beet root extract is present in 1-1500 mg, 1-1000 mg, or 1-800 mg; wherein green coffee bean extract is present in 1-1500 mg, 1-1000 mg, 1-50 mg; and/or wherein the green coffee bean extract comprises SVETOL®. The invention further comprises compositions wherein pomegranate fruit extract comprises 1-1500 mg, 1-1000 mg, or 1-8 mg and/or wherein the magnesium comprises 1-400 mg.

The invention further comprises compositions wherein the beet root extract comprises 817 mg, potassium nitrate comprises 355 mg, green coffee bean extract comprises 342 mg, and pomegranate fruit extract comprises 5 mg.

Certain embodiments further comprise calcium carbonate, microcrystalline cellulose, 15 coating (polyvinyl alcohol, macrogol, talc, titanium dioxide), stearic acid, croscarmellose sodium, magnesium stearate, or silica.

The disclosed compositions may be in the form of powders, granules, suspensions, solutions in water or non-aqueous media, capsules, sachets, gums, tablets, dissolvable oral strips; and may further comprise thickeners, flavorings, diluents, emulsifiers, dispersing aids or binders.

Included and disclosed herein are methods for improving nitric oxide levels in a subject, comprising administering to said subject, a composition comprising dietary nitrate, wherein said composition achieves, restores or maintains functional nitric oxide levels in subjects desiring to modify their nitric oxide levels by increasing salivary bioconversion of nitrate to nitrite, lowers blood pressure, and/or restores nitric oxide mediated cardiovascular benefits, including but not limited, restoring endothelium function, i.e, flow mediated dilation. The methods may involve the use of compositions as described herein. For example, in certain embodiments, the compositions comprise nitrates, wherein the dietary nitrate is derived from potassium nitrate, beet root (whole plant, powder, extract), leafy greens (including, but not limited to spinach, kale) or other nitrate-rich leafy plant portions (whole plant, powder, extract), and the compositions may enable saliva conversion of nitrate to nitrite in any elevated way. In certain embodiments, the compositions comprise the beet root extract comprising 817 mg, potassium nitrate comprising 355 mg, green coffee bean extract comprising 342 mg, and pomegranate fruit extract comprising 5 mg. The methods may comprise the use of nitrate-rich compositions wherein said compositions comprise powders, granules, suspensions, solutions in water or non-aqueous media, capsules, sachets, tablets. The methods may further involve the use of BERKELEY TEST® saliva test strips to monitor nitric oxide levels.

In alternative embodiments, disclosed compositions (optionally referred to as supplements or nutritional supplements) may include carriers, thickeners, diluents, buffers, preservatives, surface active agents, flavorings and the like in addition to the key ingredients. The supplements may also include one or more active ingredients such as magnesium, potassium, calcium and the like.

The supplements disclosed herein are preferably administered via oral routes. Compositions for oral administration include powders or granules, suspensions or solutions in water or non-aqueous media, capsules, sachets, gums, or tablets. Thickeners, flavorings, diluents, emulsifiers, dispersing aids or binders may also be incorporated. Also envisioned are oral strips that dissolve upon contact with saliva in the mouth.

In an embodiment, the novel compositions (also known as dietary supplements) as disclosed herein, comprise dietary nitrate, wherein said compositions are effective in modifying functional nitric oxide levels in a subject by increasing salivary bioconversion of nitrate to nitrite. Such compositions may be used to establish, restore and/or maintain desired nitric oxide levels. In certain embodiments, the dietary nitrate may be derived from potassium nitrate, beet plants (such as whole beet plant, beet root, beet root powder, extract), leafy greens (including, but not limited to spinach, kale, arugula) or other nitrate-rich leafy plant portions (whole plant, powder, extract). In an embodiment, the compositions comprise 1500 mg beet root extract, 1-1500 mg potassium nitrate, 1-500 mg green coffee bean extract, and 1-100 mg pomegranate fruit extract. In an embodiment, the beet root extract comprises 817 mg, potassium nitrate comprises 355 mg, green coffee bean extract comprises 342 mg, and pomegranate fruit extract comprises 5 mg. The compositions described herein may further comprise vitamin C (ascorbic acid), thiamin (thiamin mononitrate), folate (folic acid), vitamin B12 (methylcobalamin) and potassium. In certain embodiments, the compositions comprise 1-2,000 mg vitamin C (ascorbic acid), 1-800 mg thiamin (thiamin mononitrate), 1-500 mcg folate (folic acid), 1-500 mcg vitamin B12 (methylcobalamin), and 1-500 mg potassium. In certain embodiments, vitamin C (ascorbic acid) comprises 110 mg, thiamin (thiamin mononitrate) comprises 90 mg, folate (folic acid) comprises 200 mcg, vitamin B12 (methylcobalamin) comprises 200 mcg, and potassium comprises 120 mcg. Some embodiments further comprise absorbable dietary magnesium in about 1-400 mg per unit. The compositions may further comprise calcium carbonate, microcrystalline cellulose, coating (polyvinyl alcohol, macrogol, talc, titanium dioxide), stearic acid, croscarmellose sodium, magnesium stearate, silica as well as thickeners, flavorings, diluents, emulsifiers, dispersing aids or binders. The compositions may be in the form of powders, granules, suspensions, solutions in water or non-aqueous media, capsules, sachets, gums, tablets, dissolvable oral strips.

In an embodiment methods for modifying and improving nitric oxide levels in a subject, comprising administering to said subject, a composition comprising dietary nitrate, wherein said composition modifies functional nitric oxide levels in nitric oxide-deficient subjects by increasing salivary bioconversion of nitrate to nitrite, lowers blood pressure, and/or restores nitric oxide mediated cardiovascular benefits, including but not limited, restoring endothelium function, i.e, flow mediated dilation, are provided. Use of the compositions described herein result in improved cardiac health.

Effective dosages and schedules for administering the compositions/supplements may be determined empirically, and making such determinations is within the skill in the art. The dosage ranges for the administration of the supplements are those large enough to produce the desired effect in which the nitric oxide levels are modified to acceptable or desirable levels. The dosage should not be so large as to cause adverse side effects, such as unwanted cross-reactions, anaphylactic reactions, and the like. Generally, the dosage will vary with the age, condition, sex and extent of the nitric oxide levels desired, frequency of administration, or whether other drugs are included in the regimen, and can be determined by one of skill in the art. The dosage can be adjusted by individual users or by a physician in the event of any counter indications. Dosage can vary, and can be administered in one or more dose administrations daily, for one or several days. Guidance can be found in the literature for appropriate dosages for given classes of nutritional supplement products.

Following administration of the disclosed supplements, for increasing the level of nitric oxide, the efficacy of the nutritional supplement can be assessed in various ways well known to the skilled practitioner, such as an individual versed in self-monitoring. For instance, one of ordinary skill in the relevant art (i.e. an athlete) will understand that nutritional supplements as described herein are efficacious in treating or inhibiting symptoms associated with poor cardiovascular health, by observing that the supplement improves nitric oxide levels. Nitric oxide levels can be measured by methods that are known in the art, for example, using a saliva test strip such as BERKELEY TEST® to detect the presence of nitric oxide levels in saliva.

Methods of Manufacturing, Formulating and Delivering

Methods of manufacturing the nutritional or dietary supplement compositions disclosed herein, which are safe and effective in promoting nitric oxide levels in individuals, include providing the essential ingredients in accordance with the formulation noted herein and in the Examples. The essential ingredients of the subject compositions, as well as any desired inactive ingredients and/or additive ingredients are combined by weight as described above and mechanically combined, such as for example, through the use of a blender to form a blend. If necessary, the blend is then tumbled until uniform. The blend is then compressed using a tablet press to form tablets. Optionally a coating may be sprayed on the tablets and the tablets tumbled until dry. Alternatively, the blend may be placed in mineral oil to form a slurry for containment in a soft gel capsule, the blend may be placed in a gelatin capsule or the blend may be placed in other dosage forms known to those skilled in the art. Flavoring may also be added to the subject compositions/supplements to make them more palatable for oral use. Flavoring can be in a form of flavored extracts, volatile oils, chocolate flavoring, peanut butter flavoring, cookie crumbs, vanilla or any commercially available flavoring.

The dietary formulation or supplement of the invention may also contain a stabilizer such as carrageenan. carrageenan increases the viscosity of the formula without forming a gel structure, thus retarding the precipitation of insoluble calcium and phosphorus salts if included in the formula. Xanthan gum or other standard stabilizers may also be used as a stabilizer in the same fashion as carrageenan. The subject compositions are formulated to provide the above-listed essential ingredients at preferably not less than the daily dosage amounts as discussed in the Examples. This particular formulation of the subject composition has unexpectedly been shown to improve nitric oxide levels in individuals as compared to currently available supplements. The subject composition is preferably provided for oral administration in the form of lacquered tablets, unlacquered tablets, caplets or capsules. For purposes of simplicity only, throughout the remainder of this detailed description lacquered tablets, unlacquered tablets, caplets and capsules will each be referred to as simply "tablets" or "supplements" without distinction in form or function. Tablet, powders, and ideally capsules are the best means of delivery.

The preferred daily dosage of the disclosed composition as specified above may be administered in the form of one or two or more tablets. Most preferably the daily dosage of the subject composition is provided in the form of one tablet taken twice daily, for a total of two tablets a day, or in the form of two tablets taken twice daily, for a total of four tablets a day. Compared to taking the total daily dose once a day, twice daily dosing of half the total daily dose in one or more tablets per dose provides improved absorption and better maintenance of blood levels of the essential ingredients. Tablets of the preferred formulation of the subject composition contain larger quantities of essential ingredients per tablet than the minimum quantities per tablet specified above. The minimum quantities specified herein per tablet, reflect the minimum amount of each essential ingredient to be provided upon oral administration through to the date of tablet expiration as set forth on the tablet sale label. However, since essential ingredients are subject to degradation over time, the tablets may contain larger quantities of essential ingredients to compensate for ingredient degradation. By providing larger quantities of essential ingredients in each tablet, one is ensured that even with ingredient degradation, one hundred percent of the ingredient amount specified on the tablet sale label is provided upon oral administration of the tablet through to the specified expiration date of the tablet. Another consideration in formulating the subject composition is that depending on the source of the individual ingredients, individual ingredient degradation rates may vary.

Accordingly, the specific formulation of the subject composition will vary depending on the sources of the individual ingredients and the specified length of product shelf life before expiration. Typically, the product shelf life for nutritional or dietary supplements is approximately two to three years. Such ingredient overages to compensate for ingredient degradation is reflected in the preferred ingredient percentage weight per tablet information provided below. Tablet formulations may also vary somewhat depending on slight deviations from manufacturing specifications within controlled tolerance ranges as customary within the field of art.

Variations contemplated in administering the subject composition to humans or other animals include, but are not limited to, providing time-release tablets or tablets manufactured to be administered as a single dose or as other multiple part dosages. Additionally, alternative avenues of administration besides oral administration are contemplated herein such as for example, but not limited to, intraperitoneal, intravenous, subcutaneous, sublingual, transcutaneous, intramuscular or like forms of administration. Each tablet of the subject composition preferably contains the essential ingredients in the quantities specified herein, including overages to compensate for ingredient degradation.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are illustrative only, since alternative methods can be utilized to obtain similar results.

Example 1

Bioconversion of Dietary Nitrate Supplement to Nitrite, a Necessary and Required Precursor for Nitric Oxide Production within the Body FIG. 1 shows that the nitrate-rich formula bio-converts to nitrite in the oral cavity of a subject as demonstrated with salivary nitric oxide test strips. Salivary nitric oxide levels begin to rise after taking 1 or 2 servings (2 or 4 tablets) of the formula and within 2 hours post-administration optimal levels are achieved. As shown in FIG. 1, the magnitude of the nitrate to nitrite conversion is shown in the y-axis, which shows dose dependency (1 serving vs 2 servings) and the duration of the response is shown in the x-axis. The conversion of the supplement to nitrite by the oral microbiome is a critical step for the subsequent reduction of nitrite to nitric oxide within the body to maintain normal blood pressure ensure vascular homeostasis.

Formula example to promote bio-conversion within the oral cavity:

PRODUCT: NOX tablet (Berkeley Life Heart Health Supplement)

Specifications:
    Color of product—Beige
    Material type—Tablet
    Tablet shape—Modified oblong
    Tablet size—687×281 mod
    Tablet length—0.687 in
    Tablet width—0.281 in
    Weight range per 10 tablets—7.84-8.16 g
    Tablet hardness range—10-20 KP

| | mg/Tablet | % by Weight |
|---|---|---|
| Active Ingredients | | |
| BEET EXTRACT (ROOT) (*Beta vulgaris*) (25% BETAIN NITRATE) | 177.5000 | 22.1875% |
| POTASSIUM NITRATE | 171.0000 | 21.3750% |
| ASCORBIC ACID GRANULAR (95% VITAMIN C) | 60.7900 | 7.5988% |
| THIAMIN MONONITRATE (92% THIAMIN) | 58.5000 | 7.3125% |
| DECAFFEINATED GREEN COFFEE EXTRACT (GREEN BEANS) (*Coffea canephora robusta* Pierre) (50-55% POLYPHENOLS, 4550% CHLOROGENIC ACIDS, 10-15% 5-CAFFEOYLQUINIC ACID, <2% CAFFEINE) | 57.5000 | 7.1875% |
| METHYLCOBALAMIN TRITURATION (1% VITAMIN B12) | 12.0000 | 1.5000% |
| POMEGRANATE EXTRACT (FRUIT) (*Punica granatura*) (NLT 20% ELLAGIC ACID) | 2.5000 | 0.3125% |
| FOLIC ACID TRITURATION (10% FOLIC ACID) | 1.2000 | 0.1500% |
| Inactive Ingredients | | |
| SILICIFIED MICROCRYSTALLINE CELLULOSE (NUTRASOLV ® 90) | 120.0000 | 15.0000% |
| CALCIUM CARBONATE GRANULAR (NLT 37% CALCIUM) | 81.0100 | 10.1263% |
| STEARIC ACID (VEGETABLE GRADE) | 32.0000 | 4.0000% |
| CROSCARMELLOSE SODIUM | 16.0000 | 2.0000% |
| MAGNESIUM STEARATE (VEGETABLE GRADE) | 6.0000 | 0.7500% |
| SILICON DIOXIDE (SIPERNAT ®50 5) | 4.0000 | 0.5000% |
| Total weight: | 800.000 | 100.0000% |

Example 2

Reduction of LDL & Reduction of Intraocular Pressure Comprising Use of Nitrate Supplement In a study, a subject was administered the nitrate composition as disclosed herein and described in Example 1. Prior to administration, the subject exhibited significant dyslipidemia and was statin intolerance. The subject was also found to have low salivary NO bio-availability prior to the formula described in Example 1.

Prior to administration of the nitrate composition described in Example 1, the subject also developed open angle glaucoma. Prior drug treatment was found to be ineffective and intraocular pressures had started to increase showing signs of optic atrophy and surgery was being considered.

Based on high cholesterol and eye pressure, the subject was given the nitrate composition described in Example 1. Within a few hours after taking the composition, the subject showed an increase in saliva nitric oxide activity. The subject was then given the supplement for the next 90 days.

When the subject was seen 3 months later, salivary nitric oxide levels was elevated with a corresponding lowing of lipids and cardiovascular risk factors: total cholesterol was 173 mg %, LDL 79 mg %, non-HDL 72 mg %, LDL particle number by MRI was 629 nmol/L (target goal<1000), and hsCRP was normal at 0.6 mg/L.

Quite unexpectedly, the ophthalmologist had also found high salivary nitric oxide levels after 90 days with daily administration of formula in Example 1 and intraocular pressures had returned to normal. With the extended use of the formula in Example 1, eye surgery was no longer recommended.

Results

Following consumption of two nitrate composition tablets (as described in Example 1) daily for three months, the subject demonstrated:
1. significantly improved fractionated lipid levels,
2. elevated intraocular pressure was lowered and surgery was no longer being recommended.

One skilled in the art, in conjunction with research of the literature can support that there is a significant relationship to reduced nitric oxide bioavailability and increased cardiovascular risk. As demonstrated by the outcome in this Example, the unique nitrate supplement composition as disclosed, increases total body nitric oxide availability (as evidenced by, for example, the Berkeley Test® saliva nitric oxide test strip), with an associated decrease in LDL cholesterol and decrease in intraocular pressure.

An increase in sustained daily salivary nitric oxide over an extended period of time corresponded to a reduction in both LDL and intraocular pressure was not anticipated.

While the claimed nitrate dietary supplement was not given to the subject for treatment of glaucoma, the coincidental reduction in both LDL levels and ocular pressures suggest that such a formula (as described in Example 1) is an effective alternative to underperforming prescription medications, which failed in the treatment of elevated 'bad cholesterol' and glaucoma.

Conclusion

When administered over a period of three months, the novel nitrate composition described herein was effective in alleviating negative physiological effects associated with elevated blood pressure levels and related vascular complications. In particular, consumption of the novel composition by a subject suffering from elevated cholesterol levels resulted in the reduction of LDL levels whereas prior treatment with prescription medicines had failed to achieve such results. In addition, a consequence of the success demonstrating further positive results associated with the subject's improved cardiac disposition, comprised diminished intraocular pressure for the subject who was suffering from glaucoma and had experienced no alleviation in symptoms following administration of prescription statins because of intolerance.

Example 3

Nitrate Composition and Effects on Platelet Function

The disclosed nitrate compositions described herein generally, and as specifically described in Example 1, were shown to attenuate human platelet response and were shown to be useful as anti-platelet supplements. As highlighted previously, nitric oxide generation from the vascular endothelium has many beneficial effects on the cardiovascular system including a decrease in peripheral vascular resistance and inhibition of smooth muscle cell proliferation. Nitric oxide is also shown to have an anti-inflammatory and anti-thrombotic effect on endothelial cells and platelets via covalent modification of proteins involved in Weibel-Palade body exocytosis.

However, when endogenous nitric oxide production is limited, an exogenous supply of a nitric oxide donor drugs when given in large concentrations has a reported beneficial effect in critical care settings for patients with decompensated heart failure, hypertensive emergency, and pulmonary hypertension. In this example, the claimed nitrate supplement, demonstrated temporarily decreased platelet activation in multiple signal transduction pathways for which prescription medications are available, hence, the claimed supplement can be potentially useful as a natural anti-platelet agent.

Figure 2:
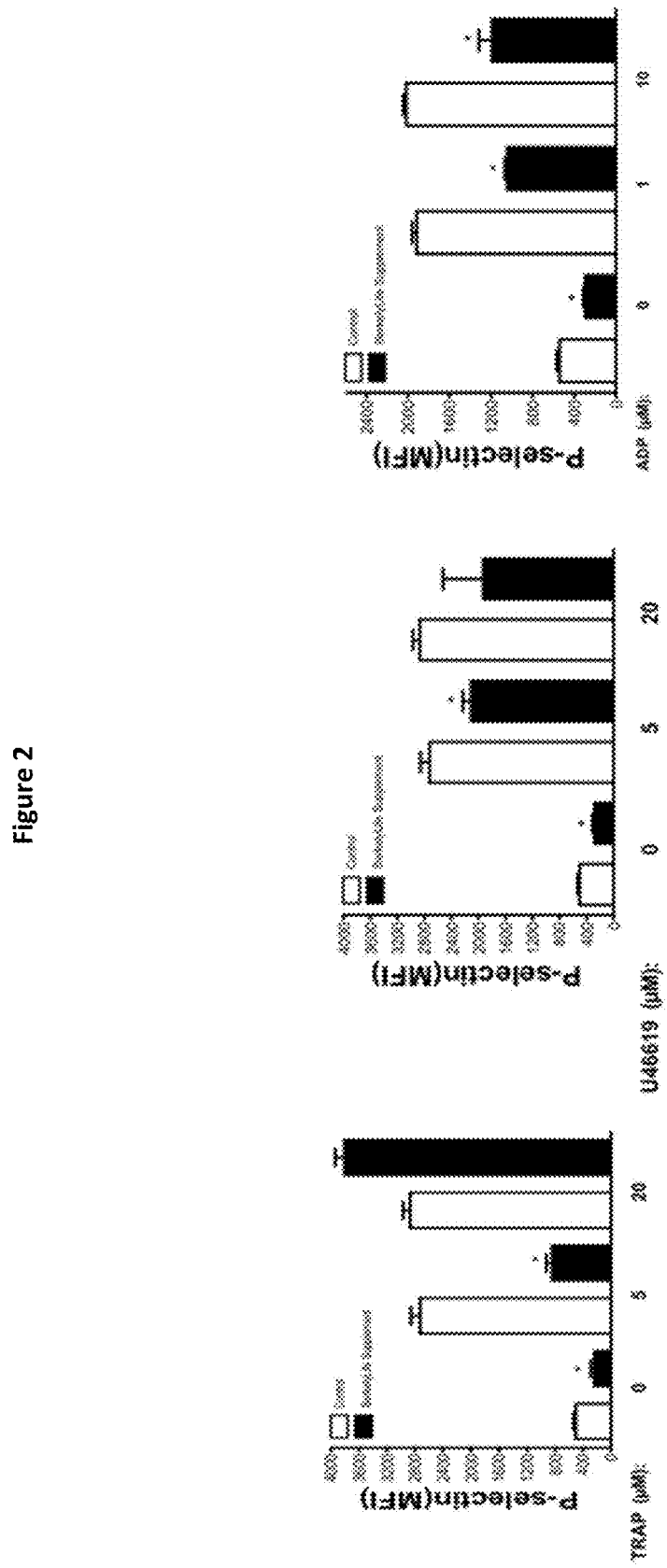
FIG. 2 provides graphs showing the effects of the compositions disclosed herein on platelet function.

FIG. 2 shows the effects of claimed dietary nitrate supplement on platelet function: A health control subject taking no medication had a venous blood draw before (control) and then 90 minutes after administration of two tablets comprising the composition as described in Example 1. Berkeley Test® saliva strips were used to show high levels of nitric oxide confirming metabolism of nitrate supplement (data not shown). Platelets isolated from a venous blood draw were stimulated with PAR1 agonist TRAP6, the thromboxane receptor agonist U46619 or P2Y12, receptor agonist 2-methyl ADP (ADP) for 15 mins and platelets activation was assessed by FACS 9P-selectin expression+/—SEM, n=4, * p, 0.01 between groups mean fluorescence intensity (MFI) was used to assess platelet function. FIG. 2 demonstrates the effects of the nitrate supplement in platelet activation in 3 different assay which support the conclusion that the formula as described in Example 1 can useful as an anti-platelet agent.

What is claimed is:

1. A composition comprising:
   1-1500 mg beet root extract;
   1-1500 mg potassium nitrate;
   1-2000 mg vitamin C;
   1-800 mg thiamin;
   1-500 mcg vitamin B12; and
   1-400 mg magnesium;
   wherein dietary nitrate is present in the composition at a concentration effective to provide 2-20 mmol nitrate per daily dose.

2. The composition of claim 1, wherein the beet root extract is present in the composition at an amount of 1-800 mg.

3. The composition of claim 1, wherein the composition is provided in the form of one or more of powders, granules, suspensions, solutions in water or non-aqueous media, sachets, gums, tablets, or dissolvable oral strips.

4. The composition of claim 1, wherein the composition is provided in the form of one or more capsules.

5. The composition of claim 4, wherein the composition is provided as two capsules.

6. A composition comprising:
   1-1500 mg beet root extract; and
   1-1500 mg potassium nitrate;
   wherein dietary nitrate is present in the composition at a concentration effective to provide 2-20 mmol nitrate per daily dose.

7. The composition of claim 6, further comprising:
   1-2000 mg vitamin C,
   1-800 mg thiamin,
   1-500 mcg vitamin B12,
   1-400 mg magnesium, or
   a combination thereof.

8. The composition of claim 6, wherein the beet root extract is present in the composition at an amount of 1-800 mg.

9. The composition of claim 6, wherein the composition is provided in the form of one or more of powders, granules, suspensions, solutions in water or non-aqueous media, sachets, gums, tablets, or dissolvable oral strips.

10. The composition of claim 6, wherein the composition is provided in the form of one or more capsules.

11. The composition of claim 10, wherein the composition is provided as two capsules.

12. The composition of claim 6, wherein the composition is effective to modify nitric oxide levels in a subject by increasing salivary bioconversion of nitrate to nitrite to at least 300 μM.

13. A method for modifying nitric oxide levels in a subject, comprising administering to the subject a composition comprising:
    1-1500 mg beet root extract; and
    1-1500 mg potassium nitrate;
    wherein dietary nitrate is present in the composition at a concentration effective to provide 2-20 mmol nitrate per daily dose.

14. The method of claim 13, wherein the composition is effective to reduce systolic blood pressure of the subject by 2-11 mmHg within 3 hrs.

15. The method of claim 14, wherein the reduced systolic blood pressure of the subject is sustained after 2 weeks.

16. The method of claim 14, wherein the reduced systolic blood pressure of the subject is sustained after 12 weeks.

17. The method of claim 13, wherein the composition is effective to modify nitric oxide levels in the subject by increasing salivary bioconversion of nitrate to nitrite to at least 300 μM.

* * * * *